United States Patent [19]

Schroeck

[11] 4,289,635

[45] Sep. 15, 1981

[54] PROCESS FOR PREPARING MOLYBDENUM-CONTAINING COMPOSITIONS USEFUL FOR IMPROVED FUEL ECONOMY OF INTERNAL COMBUSTION ENGINES

[75] Inventor: Calvin W. Schroeck, Eastlake, Ohio

[73] Assignee: The Lubrizol Corporation, Wickliffe, Ohio

[21] Appl. No.: 117,892

[22] Filed: Feb. 1, 1980

[51] Int. Cl.³ .............................................. C10M 1/48
[52] U.S. Cl. .......................... 252/32.7 E; 252/32.7 R; 252/18; 252/25; 260/429 R
[58] Field of Search .................... 252/32.7 E, 32.7 R, 252/18, 25; 260/429 R

[56] References Cited

U.S. PATENT DOCUMENTS

| | | | |
|---|---|---|---|
| 3,223,625 | 12/1965 | Cyphers et al. | 252/18 |
| 3,256,184 | 6/1966 | Harting et al. | 252/32.7 E |
| 3,400,140 | 9/1968 | Rowan et al. | 260/429 |
| 3,494,866 | 2/1970 | Rowan et al. | 252/32.7 E |
| 3,840,463 | 10/1974 | Froeschmann et al. | 252/42.7 |
| 3,926,822 | 12/1975 | Habiby | 252/48.6 |
| 3,953,347 | 4/1976 | Habiby | 252/48.6 |
| 4,119,549 | 10/1978 | Davis | 252/45 |
| 4,119,550 | 10/1978 | Davis et al. | 252/45 |
| 4,175,043 | 11/1979 | Horodysky | 252/32.7 E |

Primary Examiner—Paul F. Shaver

Attorney, Agent, or Firm—Ronald L. Lyons; William H. Pittman; Raymond F. Keller

[57] ABSTRACT

Molybdenum-containing compositions prepared by reacting an olefinically unsaturated compound capable of reacting with active sulfur with a composition prepared by reacting:

(a) a phosphorus-containing acid represented by the formula:

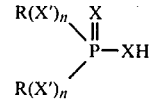

wherein each X and X' is independently oxygen or sulfur, each n is zero or one and each R is independently the same or a different hydrocarbon-based radical; and (b) at least one hexavalent molybdenum oxide compound, and (c) hydrogen sulfide, in the presence of (d) a polar solvent are useful as additives for lubricants. Internal combustion engines, especially gasoline engines, when lubricated by said additive-containing lubricants exhibit improved fuel economy.

82 Claims, No Drawings

PROCESS FOR PREPARING MOLYBDENUM-CONTAINING COMPOSITIONS USEFUL FOR IMPROVED FUEL ECONOMY OF INTERNAL COMBUSTION ENGINES

BACKGROUND OF THE INVENTION

1. Field of the Invention

This invention relates to sulfur-, phosphorus- and molybdenum-containing compositions made from phosphorus-containing acids. This invention also relates to sulfur-, phosphorus- and molybdenum-containing compositions having reduced sulfur activity. More specifically this invention relates to processes for preparing these sulfur-, phosphorus- and molybdenum-containing compositions, which are useful as additives in lubricants. Additionally, this invention relates to concentrates of these compositions and to lubricant compositions comprising these compositions. This invention also relates to a method for reducing fuel consumption by lubricating an internal combustion engine with these lubricating compositions.

2. Description of the Prior Art

Sulfur-containing molybdenum salts of phosphorus-containing acids and processes for preparing said compositions have been described in U.S. Pat. Nos. 3,223,625; 3,256,184; 3,400,140; 3,494,866; 3,840,463, and 4,156,099. These U.S. Patents are hereby incorporated by reference for their disclosures in this regard.

A principal object of the present invention is to provide novel sulfur-, phosphorus- and molybdenum-containing compositions made from phosphorus-containing acids as well as processes for making them.

Another object is to provide novel sulfur-, phosphorus- and molybdenum-containing compositions having reduced active sulfur made from phosphorus-containing acids.

Still another object is to provide novel sulfur-, phosphorus- and molybdenum-containing compositions made from phosphorus-containing acids which exhibit friction reducing properties in lubricants.

An additional object is to provide novel concentrates comprising these novel sulfur-, phosphorus- and molybdenum-containing compositions.

Another additional object is to provide novel lubricant compositions containing these novel, friction-reducing, sulfur-, phosphorus- and molybdenum-containing compositions.

A further object is to provide a novel method for reducing fuel consumption by lubricating an internal combustion engine with these novel, friction-reducing, sulfur-, phosphorus- and molybdenum-containing compositions.

These and other objects of this invention are accomplished by providing a process for preparing a composition which comprises reacting an olefinically unsaturated compound capable of reacting with active sulfur with a composition prepared by a process which comprises reacting:

(a) A phosphorus-containing acid represented by the formula:

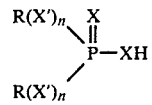

wherein each X and X' is independently oxygen or sulfur, each n is zero or one, and each R is independently the same or different hydrocarbon-based radical;

(b) at least one hexavalent molybdenum oxide compound, and (c) hydrogen sulfide, in the presence of (d) a polar solvent.

Typical phosphorus-containing acids (a) from which the compositions of this invention can be made are known. Illustrative examples of some preferred phosphorus- and sulfur-containing acids are:

1. Dihydrocarbylphosphinodithioic acids, such as amylphosphinodithioic acid, corresponding to the formula,

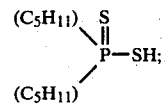

2. S-hydrocarbyl hydrogen hydrocarbylphosphonotrithioates, such as S-amyl hydrogen amylphosphonotrithioate, corresponding to the formula,

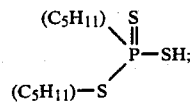

3. O-hydrocarbyl hydrogen hydrocarbylphosphonodithioates, such as O-amyl hydrogen amylphosphonodithioate, corresponding to the formula,

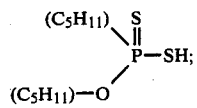

4. S,S-dihydrocarbyl hydrogen phosphorotetrathioates, such as diamyl hydrogen phosphorotetrathioate, corresponding to the formula,

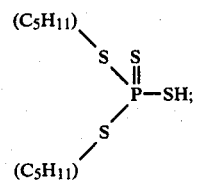

5. O,S-dihydrocarbyl hydrogen phosphorotrithioates, such as O,S-diamyl hydrogen phosphorotrithioate, corresponding to the formula,

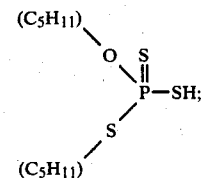

6. O,O-dihydrocarbyl hydrogen phosphorodithioates, such as O,O-diamyl hydrogen phosphorodithioate, corresponding to the formula,

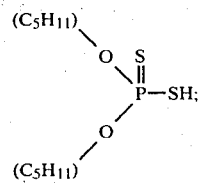

Preferred acids of the formula

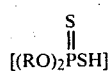

are readily obtainable from the reaction of phosphorus pentasulfide (P$_2$S$_5$) and an alcohol or a phenol. The reaction involves mixing at a temperature of about 20° to about 200° C., 4 moles of the alcohol or a phenol with one mole of phosphorus pentasulfide. Hydrogen sulfide is liberated in this reaction. The oxygen-containing analogs of these acids are conveniently prepared by treating the dithioic acid with water or steam which, in effect, replaces one or both of the sulfur atoms.

Thus, as previously mentioned, the preferred phosphorus-containing acids are phosphorus- and sulfur-containing acids. These preferred acids more preferably include those of the above formula wherein at least one X is sulfur, more preferably both of X are sulfur; at least one X' is oxygen or sulfur, more preferably both of X' are oxygen and n is 1. Mixtures of acids may be employed according to this invention.

The terminology of "hydrocarbon-based radical" as used herein, ("herein" includes the appended claims) is used to define a substantially saturated monovalent radical derived from a hydrocarbon by removal of a hydrogen from a carbon atom of the hydrocarbon. This carbon atom is directly connected to the remainder of the molecule. These hydrocarbon-based radicals are derived from aliphatic hydrocarbons, cyclo-aliphatic hydrocarbons, aromatic hydrocarbons, mixed aliphatic-cyclo-aliphatic hydrocarbons, mixed aliphatic aromatic hydrocarbons, and mixed cyclo-aliphatic-aromatic hydrocarbons. Therefore, these hydrocarbon-based radicals would be referred to as aliphatic-based radicals, cyclo-aliphatic based radicals, etc. The base hydrocarbons from which these radicals are derived may contain certain non-reactive or substantially non-reactive polar or non-hydrocarbon substituents.

The terminology "substantially saturated" as used herein is intended to define radicals free from acetylenic unsaturation (—C≡C—) in which there is not more than one ethylenic linkage (—C=C—) for every 10 carbon-to-carbon (preferably 20) covalent bonds. The so-called "double bonds" in the aromatic ring (e.g., benzene) are not to be considered as contributing to unsaturation with respect to the terminology "substantially saturated". Usually there will be no more than an average of one ethylenic linkage per substantially saturated monovalent radical as described hereinbefore. Preferably, (with the exception of aromatic rings) all the carbon-to-carbon bonds in a substantially saturated radical will be saturated linkages; that is, the radical will be free from acetylenic and ethylenic linkages.

In general, the hydrocarbon-based radical may contain up to about 30 carbon atoms with a preferred range of carbon atoms being from one to about 20. The hydrocarbon-based radicals may contain certain non-reactive or substantially non-reactive polar or non-hydrocarbon substituents which do not materially interfere with the reactions or compositions herein, as will be recognized by those skilled in the art. Representative non-hydrocarbon or polar substituents include halo substituents, such as chloro, fluoro, bromo and iodo; nitro; lower alkoxy, such as butoxy and hexyloxy; lower alkyl thio, such as pentylthio and heptylthio; hydroxy; mercapto;

hydrocarbyl, e.g.,

lower alkyl; hydrocarbyl

hydrocarbon and the like. As a general rule, and particularly when the compositions of this invention are to be used as lubricant additives, the degree of substitution and nature of the substituent of the hydrocarbon-based radical is such that the predominantly hydrocarbon character of the radical is not destroyed. Thus, in view of this requirement, these radicals normally have no more than four substituents per radical, and usually, not more than one substituent for every 10 carbon atoms in the radical. Preferably, the hydrocarbon-based radical is a purely hydrocarbyl (i.e., a hydrocarbon radical containing only carbon and hydrogen atoms).

The term "lower" when used herein to denote radicals such as lower alkyl is intended to describe a radical containing up to seven carbon atoms.

Desirable compositions of this invention include those made from phosphorus-containing acids wherein each R is hydrocarbyl, particularly, independently alkyl, aryl, alkaryl and arylalkyl of up to about 30 carbon atoms, more preferably from three to about 20 carbon atoms. The preferred R groups are alkyl and alkaryl, preferably alkyl.

The hexavalent molybdenum oxide compounds (b) useful for this invention are water-soluble hexavalent molybdenum oxide compounds which are acidic under aqueous conditions. The aqueous chemistry of hexavalent molybdenum oxide compounds is well known to those of ordinarily skill in the art and further discussion is not necessary.

These acidic water-soluble hexavalent molybdenum compounds can be obtained from molybdenum trioxide-containing compounds or mixtures of two or more of these compounds.

These molybdenum trioxide-containing compounds include molybdenum trioxide (MoO$_3$) and compounds that are made from molybdenum trioxide. The molybdenum trioxide-containing compounds include MoO$_3$, molybdenum trioxide hydrates, molybdic acid, ammonium molybdate, alkali metal molybdates (e.g., sodium or potassium) and heteropolyacid molybdates (e.g., phosphomolybdic acid).

The preferred acidic water-soluble hexavalent molybdenum oxide compounds are molybdenum trioxide; molybdic acid; the heteropolyacid molybdates, especially the phosphomolybdates; those generated by acidification of alkali metal molybdates or ammonium molybdates with, e.g., hydrochloric acid, acetic acid or sulfuric acid; and those generated in an aqueous solution of $MoO_3$ or its hydrates, wherein the solubility in water of the $MoO_3$ or its hydrates has been enhanced by the addition of an acid or base.

Also useful as (b) are the hexavalent molybdenum oxyhalides such as $MoOCl_4$, $MoO_2Cl_2$, $MoO_2Br_2$, $Mo_2O_3Cl_6$, $MoOF_4$ and mixtures thereof which can be hydrolyzed by water to the acidic water-soluble hexavalent molybdenum oxide compounds.

A more detailed discussion of the nature of molybdenum trioxide-containing compounds, particularly concerning the description, preparation, acidity and water solubility of these compounds, can be found in D. H. Killeffer and A. Linz, *Molybdenum Compounds, Their Chemistry and Technology*, Interscience Publishers, New York, 1952, Chapters 4, 6, 7 and 8; and F. A. Cotton and G. Wilkinson, *Advanced Inorganic Chemistry, A Comprehensive Text*, 2nd Edition, Interscience Publisher—A division of John Wiley and Sons, New York, London, Sidney, 1966, pages 930–960, which are hereby incorporated by reference for their disclosures in this regard.

Normally the hexavalent molybdenum compound (b) or its precursor is dispersed or dissolved in a polar solvent (d). Alternatively, (a) and (b) or their precursors may be first combined followed by the addition of (d). In some situations it may be desirable to generate (a) and/or (b) in situ, preferably in the presence of (d). In the case of (a), for example, a metal salt of the phosphorus-containing acid (e.g., alkali metal) could be acidified in the presence of (b) to yield (a). In the case of (b), for example, a molybdenum trioxide-containing compound can be used to generate an acidic water-soluble hexavalent molybdenum compound by acidifying an alkali metal molybdate in the presence of (a) and (d) to generate (b) in situ.

For the purpose of this invention it is necessary that a reaction mixture of (a) and (b) be first prepared, preferably in the presence of (d), before reaction with hydrogen sulfide (c).

Hydrogen sulfide (c) is commercially available and can be introduced into the reaction chamber either above or below the surface of the reaction mixture of (a) and (b) in the presence of (d).

Another source can be $H_2S$ generated in situ. For example, alkali metal sufides, e.g., $Na_2S$, could be acidified with HCl to generate in $H_2S$ in the presence of (a), (b) and (d).

The polar solvent (d) useful in this invention includes water, organic polar solvents such as alcohols, ethers, ketones, and mixtures thereof. The preferred polar solvent (d) is water and mixtures of water and one or more other organic polar solvents. The preferred organic polar solvents are the lower alkyl alcohols, ethers and ketones.

In addition to the polar solvents, the reaction may be carried out in the presence of a substantially inert liquid solvent/diluent medium. This solvent/diluent medium desirably serves to maintain contact of the reactants and facilitate control of the reaction temperatures. Examples of suitable solvent/diluent media include aliphatic and aromatic hydrocarbons as benzene, toluene, naphtha, mineral oil, hexane; chlorinated hydrocarbons as dichlorobenzene and heptylchloride.

As used in the specification and the appended claims, the term "substantially inert" when used to refer to solvents/diluents, and the like, is intended to mean that the solvent/diluent, etc., is sufficiently inert to chemical or physical change under the conditions in which it is used so as not to materially interfere in an adverse manner with the preparation, storage, blending and/or functioning of the compositions, additive, compound, etc., of this invention in the context of its intended use. For example, small amounts of a solvent/diluent, etc. can undergo minimal reaction or degradation without preventing the making and using of the invention as described herein. In other words, such reaction or degradation, while technically discernible, would not be sufficient to deter the practical worker of ordinary skill in the art from making and using the invention for its intended purposes. "Substantially inert" as used herein is, thus, readily understood and appreciated by those of ordinary skill in the art.

As used in this specification and the appended claims, the term "solvent/diluent medium" is intended to include those solvent/diluent media in which independently each of the reactants are soluble or stably dispersible. The term "stably dispersible" as used in the specification and the appended claims is intended to mean a composition (e.g., a single compound, a mixture of two or more compounds, etc.) is capable of being dispersed in a given medium to an extent which allows it to function in its intended manner. Thus, for example, where a composition is prepared by a reaction in an oil, it is sufficient that the reactants be capable of being suspended in the oil in a manner sufficient to allow the reaction to occur and the formation of the composition. Thus, the term "solvent/diluent medium" is understood and can be used in a conventional manner by those of ordinary skill in the art.

The product of reacting components (a), (b) and (c) in the presence of (d) may be used as a lubricant additive, however, it is preferred that (d) be removed particularly when (d) is water. The compositions made by reacting (a), (b) and (c) in the presence of (d) sometimes may be accompanied by the formation of by-products and/or excess solvent/diluent medium which may lessen its commercial appeal. Accordingly, the polar solvent (d), undesirable by-products and/or excess or undesired solvent/diluent medium can be separated from the compositions of this invention by techniques known in the art, e.g., filtration, evaporation (e.g., stripping), etc., to obtain a more desirable product. Alternatively, if the solvent/diluent medium is, for example, a base oil suitable for use in the lubricating compositions of this invention, the product can be left in the solvent/diluent medium and used to form the lubricating compositions as described below.

Another aspect which in some cases might lessen the commercial appeal of the compositions made by reacting (a), (b) and (c) in the presence of (d) is the highly active sulfur contained in these compositions. This high activity sulfur is generally referred to as corrosive or active sulfur. This active sulfur is very reactive and is corrosive towards metals such as copper and silver. Therefore, reduction in the active sulfur in a composition will result in that composition being less corrosive towards metals. Active sulfur is well known to those of ordinary skill in the art and further discussion thereof is not necessary.

The activity of the sulfur contained in the compositions made by reacting (a), (b) and (c) in the presence of (d) can be reduced by reacting these compositions with one or more olefinically unsaturated compounds capable of reacting with active sulfur.

The olefinically unsaturated compounds which react with the highly active sulfur contained in the compositions made by reacting (a), (b) and (c) in the presence of (d) are diverse in nature. They contain at least one olefinic double bond, which is defined as a non-aromatic double bond; that is, one connecting two aliphatic carbon atoms. In its broadest sense, the olefin may be defined by the formula $R_1R_2C=CR_3R_4$, wherein each of $R_1$, $R_2$, $R_3$ and $R_4$ is hydrogen or an organic radical. In general, the R groups in the above formula which are not hydrogen may be satisfied by such groups as $-C(R^5)_3$, $-COOR^5$, $-CON(R^5)_2$, $-COON(R^5)_4$, $-COOM$, $-CN$,

$R^5$, $-X$, $-YR^5$ or $-Ar$, wherein:

Each $R^5$ is independently hydrogen, alkyl, alkenyl, aryl, substituted alkyl, substituted alkenyl or substituted aryl, with the proviso that any two $R^5$ groups can be alkylene or substituted alkylene whereby a ring of up to about 12 carbon atoms is formed;

M is one equivalent of a metal cation (preferably Group I or II, e.g., sodium, potassium, barium, calcium);

X is halogen (e.g., chloro, bromo, or iodo);

Y is oxygen or divalent sulfur;

Ar is an aryl or substituted aryl radical of up to about 12 carbon atoms in the substituent.

Any two of $R^1$, $R^2$, $R^3$ and $R^4$ may also together form an alkylene or substituted alkylene group; i.e., the olefinic compound may be alicyclic.

The natures of the substituents in the substituted moieties described above are not normally a critical aspect of the invention and any such substituent is useful so long as it is or can be made compatible with lubricating environments and does not interfere under the contemplated reaction conditions. Thus, substituted compounds which are so unstable as to deleteriously decompose under the reaction conditions employed are not contemplated. However, certain substituents such as keto or aldehydo can desirably undergo sulfurization. The selection of suitable substituents is within the skill of the art or may be established through routine testing. Typical of such substituents include any of the above-listed moieties as well as hydroxy, amidine, amino, sulfonyl, sulfinyl, sulfonate, nitro, phosphate, phosphite, alkali metal mercapto and the like.

The olefinically unsaturated compound is usually one in which each R group which is not hydrogen is independently alkyl, alkenyl or aryl, or (less often) a corresponding substituted radical. Monoolefinic and diolefinic compounds, particularly the former, are preferred, and especially terminal monoolefinic (α-olefins) hydrocarbons; that is, those compounds in which $R^3$ and $R^4$ are hydrogen and $R^1$ and $R^2$ are alkyl or aryl, especially alkyl (that is, the olefin is aliphatic). Olefinic compounds having from about 8 up to about 36 and especially from about 8 up to about 20 carbon atoms are particularly desirable.

The $C_{8-36}$ aliphatic α-olefin (i.e., terminal olefin) is usually one which is unbranched on the olefinic carbon atoms; that is, which contains the moiety $CH_2=CH-$. It also usually contains substantially no branching on the allylic carbon atoms; that is, it preferably contains the moiety $CH_2=CHCH_2-$. The preferred olefins are those in the $C_{8-20}$ range. Mixtures of these olefins are commercially available and such mixtures are suitable for use in this invention.

Also, fatty acid esters derived from one or more unsaturated carboxylic acids are particularly useful as the olefinically unsaturated compounds.

The term "fatty acid" as used herein refers to acids which may be obtained by hydrolysis of a naturally occurring vegetable or animal fat or oil. These are usually in the $C_{16-20}$ range and include oleic acid, linoleic acid and the like.

Fatty acid esters which are useful are primarily esters of aliphatic alcohols, including monohydric alcohols such as methanol, ethanol, n-propanol, isopropanol, the butanols, etc., and polyhydric alcohols including ethylene glycol, propylene glycol, trimethylene glycol, neopentyl glycol, glycerol and the like. Particularly preferred are fatty oils derived predominantly from unsaturated acids, that is, naturally occurring triglycerides of long chain unsaturated carboxylic acids, especially linoleic and oleic acids. These fatty oils include such naturally occurring animal and vegetable oils as lard oil, peanut oil, cotton seed oil, soybean oil, corn oil and the like.

The composition and nature of fatty oils is well known to those of ordinary skill in the art and can be found in more detail in M. P. Doss, *Properties of the Principal, FATS, Fatty Oils, Waxes, Fatty Acids and Their Salts*, The Texas Company, 1952, which is hereby incorporated by reference for its description of the fatty oils and unsaturated carboxylic acids useful for this invention.

A reaction mixture of (a) and (b) must first be prepared before reaction with (c) in the presence of (d). It is preferred that (d) is present when preparing the reaction mixture of (a) and (b); and it is particularly preferred to disperse or dissolve (b) in (d) before contact with (a). This reaction mixture may be conveniently prepared within a temperature range of from about 0° up to about 150° C., preferably from about 25° C. up to about 100° C.

The reaction of (a), (b) and (c) in the presence of (d) may be conveniently carried out at within the temperature range of about 0°–150° C. Although it is not necessary, it is preferred to control the temperature so that it is reasonably constant throughout the course of the reaction. It is particularly preferred to control the temperature within the range of from about 50° C. up to about 100° C.

The reaction of the compositions prepared by reacting (a), (b) and (c) in the presence of (d) with the olefinically unsaturated compounds capable of reacting with active sulfur may be conveniently carried out in a temperature range of from about 100° C. up to about 150° C., preferably from about 110° C. up to about 140° C.

The period of time for reaction varies with several factors including nature and amount of reactants, reaction equipment, solvent/diluent medium, degree of mixing, and the like.

For the purposes of this invention, the molecular weight of a phosphorus-containing acid (a) is equal to its equivalent weight and, therefore, one mole of (a) is equal to its equivalent weight, which is determined by substituting its "acid number" in the following equation:

$$\text{Equivalent weight} = \frac{56,100 \text{ milligrams of KOH/equivalent}}{\text{acid number (milligrams of KOH/gram)}}$$

The "acid number" is defined as the number of milligrams of KOH used to raise the pH of one gram of sample under aqueous conditions to about 4.0. The pH of about 4.0 can be determined by the use of an indicator that changes color in the range of 3.0 to 4.5 such as bromphenol blue or by electrical means such as a pH-meter.

For the purposes of this invention, the ratio of reactants (a) to be is about 0.5 up to about four moles of the phosphorus-containing acid (a) per mole of molybdenum in (b) (e.g., one mole of $Na_2MoO_4$ contains one mole of molybdenum; ammonium paramolybdate, $(NH_4)_6Mo_7O_{24}\cdot 4H_2O$, contains seven moles of molybdenum). A ratio of at least about 0.5 mole of hydrogen sulfide per mole of molybdenum in the reaction mixture of (a) and (b) is desirable.

Therefore, the range ratios of (a):(b):(c) is from about 0.5 up to about four moles of (a):one mole of molybdenum in (b):at least 0.5 mole of $H_2S$. A ratio of about 1:1:1.5 is optimum, although an excess (i.e., 1:1:>1.5) of hydrogen sulfide can be used to insure complete reaction. A ratio of 1:1:4 or more may be used, but a ratio of 1:1:2 should be sufficient to insure complete reaction. Excess hydrogen sulfide can be removed by blowing the reaction mixture with an inert gas such as nitrogen.

The preferred amount of olefinically unsaturated compound useful for the purposes of this invention is the minimum amount necessary to react with all of the active sulfur present in the composition prepared by reacting (a), (b) and (c) in the presence of (d).

It is believed that for every 1.5 moles of hydrogen sulfide (c) used per mole of molybdenum in (b), 0.5 mole of active sulfur is generated in the reaction of (a), (b) and (c) in the presence of (d). Also, one olefinic double bond is capable of reacting with two moles of active sulfur.

Therefore, the minimum amount of olefinically unsaturated compound necessary is based on the stoichiometric relationship of one olefin double bond for every two moles of active sulfur generated. Although this ratio describes the reaction stoichiometrically, lesser or greater amounts of olefinically unsaturated compound can be used as the situation demands. For example, greater amounts (stoichiometric excesses) of the olefinically unsaturated compound will normally be used to increase the rate of reaction and insure complete reaction of active sulfur.

The polar solvent (d) is essentially a promotor or contact agent. Therefore, minimum amount of polar solvent (d) is that amount necessary for the reaction of (a), (b) and (c) to proceed (i.e., the point at which the hydrogen sulfide will react with (a) and (b) in the presence of (d). Generally, ehough (d) is used to disperse or, preferably dissolve the molybdenum trioxide containing compounds or the molybdenum-oxyhalide compounds previously described. Usually from about one up to about four parts of (d) will be used for each part by weight of the above-described molybdenum compound used. Substantial amounts of (d) in excess of this would not be uncommon, but would not be advantageous.

This invention is exemplified in the following examples. Of course, these examples are not intended to limit this invention as modification of the examples by ordinary expedients will be readily apparent to those of ordinary skill in the art.

In all examples, unless otherwise stated, all temperatures are in °C.; all parts are parts by weight and all percentages are derived from parts by weight.

EXAMPLE 1

A reaction mixture is prepared by the addition of 2035 parts (9.17 moles) of $P_2S_5$ to 7335 parts (36.68 moles) of a commercially available $C_{12-14}$ alcohol at 80° C. under a nitrogen blanket. The $P_2S_5$ is added over a two-hour period and the exotherm increases the temperature to 95° C. during the addition period. The hydrogen sulfide formed as a result of the reaction is removed continuously and trapped by caustic soda solution. The reaction mixture is allowed to cool while stirring for two hours under nitrogen. The reaction mixture is filtered to yield the desired O,O-di-$C_{12-14}$ phosphorodithioic acid which has an acid number of 96.

EXAMPLE 2

The procedure for Example 1 is repeated except the $C_{12-14}$ alcohol is replaced on an equimolar basis with 2-ethylhexyl alcohol to yield the desired O,O-di-2-ethylhexyl phosphorodithioic acid which has an acid number of 137.

EXAMPLE 3

A reaction mixture is prepared by adding a mixture of 584 parts (1 mole) of the O,O-di-$C_{12-14}$ phosphorodithioic acid prepared in Example 1 and 500 parts of toluene to a room temperature (26° C.) solution of 40 parts (1 mole) of sodium hydroxide, 190 parts of water and 144 parts (1 mole) of molybdenum trioxide prepared by heating until a clear solution is obtained. After the addition is complete, 100 parts (1 equivalent) of concentrated hydrochloric acid is added to the reaction mixture. The reaction mixture is heated at 40° C. for two hours.

Hydrogen sulfide (90 parts; 2.6 moles) is added to the reaction mixture by subsurface addition over a period of three hours. During the hydrogen sulfide addition, the temperature of the reaction mixture is increased to 90° C.

The reaction mixture is then purged of excess hydrogen sulfide by blowing with nitrogen, stripped under vacuum at 94° C. and filtered to yield the desired sulfur-, phosphorus- and molybdenum-containing composition made from O,O-di-$C_{12-14}$ phosphorodithioic acid.

EXAMPLE 4

A reaction mixture is prepared by the addition of 3,275 parts (8 moles) of the O,O-di-2-ethylhexylphosphorodithioic acid prepared in Example 2 to a room temperature slurry of 1,152 parts (8.0 moles) of molybdenum trioxide in 2,000 parts of water. The reaction mixture is heated to 80° C. and 533 parts hydrogen sulfide is added by subsurface addition over a 6.5-hour period. The reaction mixture is maintained at 80°-90° C. during the hydrogen sulfide addition. The reaction mixture is then purged of excess hydrogen sulfide by blowing with nitrogen and stripped at 95°-100° C. under vacuum to yield the residue as the desired sulfur-, phosphorus- and molybdenum-containing composition made from an O,O-di-2-ethylhexylphosphorodithioic acid.

EXAMPLE 5

An aqueous solution of phosphomolybdic acid is prepared by heating 360 parts (2.5 moles) of molybdenum trioxide, 24 parts of 85% phosphoric acid and 2,000 parts of water at boiling for three hours, then filtering through filter paper and washing the residue with 150 parts of water. The total volume of the resulting solution is reduced to yield 921 parts of solution containing 19.37% molybdenum.

EXAMPLE 6

A reaction mixture is prepared by the dropwise addition of 1,475 parts (3.0 moles) of the phosphomolybdic acid prepared in Example 5 to 1,228 parts (3 moles) of the O,O-di-2-ethylhexylphosphorodithioic acid prepared in Example 2 at room temperature over a one-hour period. The reaction mixture is then held at 55° C. for 3.5 hours. The reaction mixture is heated to reflux while blowing with hydrogen sulfide beneath the surface. The reaction mixture is held at 90°-95° C. for three hours during which hydrogen sulfide blowing is continued. A total of 242 parts of hydrogen sulfide is added to the reaction mixture. The reaction mixture is then purged of excess hydrogen sulfide by blowing with nitrogen. Toluene (1000 parts) is added to the reaction mixture and water is removed by azeotropic distillation. The reaction mixture is filtered and then stripped of toluene at 95° C. under vacuum to yield the desired sulfur-, phosphorus- and molybdenum-containing composition made from an O,O-di-2-ethylhexylphosphorodithioic acid.

EXAMPLE 7

A reaction mixture is prepared by adding a mixture of 2050 parts (5.0 moles) of the O,O-di-2-ethylhexylphosphorodithioic acid prepared in Example 2 and 2,500 parts of toluene to a room temperature solution prepared by heating parts (5 moles) of sodium hydroxide, 1,000 parts of water and 720 parts (5.0 moles) of molybdenum trioxide until a clear solution is obtained and then adding 39 parts (0.25 mole) of 85% phosphoric acid to the solution. After addition is complete, 500 parts (5 moles) of concentrated hydrochloric acid is added to the reaction mixture and the mixture is then heated at 40° C. for two hours. Hydrogen sulfide (318 parts; 9.35 moles) is added to the reaction mixture by subsurface addition over a period of ten hours. During the hydrogen sulfide addition, the temperature of the reaction mixture is increased to reflux. The reaction mixture is then purged of excess hydrogen sulfide by blowing with nitrogen and stripped under vacuum at 90° C. Toluene (2,000 parts) is added to the reaction mixture which is filtered and then stripped to yield the desired sulfur-, phosphorus- and molybdenum-containing composition made from an O,O-di-2-ethylhexylphosphorodithioic acid.

EXAMPLE 8

A reaction mixture of 1,152 parts (8 moles) of molybdenum trioxide, 77 parts (0.67 mole) of 85% phosphoric acid, 3,000 parts of water and 3,275 parts (8 moles) of O,O-di-2-ethylhexylphosphorodithioic acid prepared in Example 2 is heated to 85° C. To the reaction mixture 533 parts of hydrogen sulfide is added by subsurface addition over a 6.5-hour period. The reaction mixture is maintained at 80°-90° C. during the hydrogen sulfide addition. The reaction mixture is then purged of excess hydrogen sulfide by blowing with nitrogen and stripped at 95°-100° C. under vacuum to yield the residue as the desired sulfur-, phosphorus- and molybdenum-containing composition made from an O,O-di-2-ethylhexyl-phosphorodithioic acid.

EXAMPLE 9

A reaction mixture of 4557 parts of the sulfur-, phosphorus- and molybdenum-containing composition prepared in Example 4 and 1,137 parts of a commercially available mixture of $C_{15-18}$ α-olefins is heated at 130° C. for three hours. The reaction mixture is filtered to yield the desired product.

EXAMPLE 10

The procedure for Example 9 is repeated except the $C_{15-18}$ α-olefin is replaced by a mixture of 1,139 parts of a commercially available soybean oil and 681 parts of a commercially available mixture of $C_{15-18}$ α-olefins.

EXAMPLE 11

The procedure for Example 10 is repeated except the sulfur-, phosphorus- and molybdenum-containing composition is replaced on an equal weight basis by the molybdenum-containing composition prepared in Example 6.

EXAMPLE 12

A reaction mixture of 446 parts of the sulfur-, phosphorus- and molybdenum-containing composition prepared in Example 3, 73 parts of commercially available soybean oil and 34 parts of a commercially available mixture of $C_{15-18}$ α-olefins is heated at 125°-135° C. for six hours. The reaction mixture is diluted with 2,500 parts of toluene and filtered. The filtrate is stripped to yield the desired product.

As previously indicated, the compositions of this invention are also useful as additives for lubricants, in which they function primarily as oxidation, inhibitors, antiwear and/or extreme pressure agents and friction modifiers. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metalworking lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes (e.g., dodecylbenzenes, tetradecylbenzenes, dinonylbenzenes, di(2-ethylhexyl)benzenes, etc.); polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)-siloxanes, poly-(methylphenyl)siloxanes, etc.). Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the composition of this invention sufficient to provide it with improved oxidation stability and/or antiwear and/or extreme pressure and/or friction reducing properties. Normally this amount will be about 0.05% to about 20%. Preferably about 0.1% to about 10%, more preferably up to about 5% and typically about 0.5% up to about 2% of the total weight of the lubricant. In lubricating oils operated under extremely adverse conditions, such as lubricating oils for marine diesel engines, the reaction products of this invention may be present in amounts of up to about 30% by weight.

The invention also contemplates the use of other additives in combination with the compositions of this invention. Such additives include, for example, auxiliary detergents and dispersants of the ash-producing or ashless type, corrosion- and oxidation-inhibiting agents, pour point depressing agents, extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, postassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkyphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-$\beta$-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Auxiliary ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen-containing compounds such as amine, organic hydroxy compounds such as phenols and alcohols, and/or basic inorganic materials. Examples of these "carboxylic dispersants" are described in British Pat. No. 1,306,529 and in many U.S. patents including the following U.S. Pat. Nos.:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of relatively high molecular weight aliphatic or alicyclic halides with amines, preferably polyalkylene polyamines. These may be characterized as "amine dispersants" and examples thereof are described for example, in the following U.S. Pat. Nos.:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Pat. Nos. are illustrative:

| | |
|---|---|
| 3,413,347 | 3,725,480 |
| 3,697,574 | 3,726,882 |
| 3,725,277 | |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos.:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos.:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain about 20–90% by weight of the composition of this invention and may contain, in addition, one or more other additives known in the art or described hereinabove.

The lubricating compositions made according to this invention can be exemplified by a lubricating composition prepared by treating a mineral oil of lubricating viscosity with 1% by weight of the product of Example 9.

What is claimed is:

1. A process for preparing a composition which comprises reacting an olefinically unsaturated compound capable of reacting with active sulfur with a composition prepared by a process which comprises reacting:

(a) A phosphorus-containing acid represented by the formula:

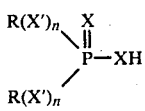

wherein each X and X' is independently oxygen or sulfur, each n is zero or one, and each R is independently the same or a different hydrocarbon-based radical;
(b) at least one hexavalent molybdenum oxide compound, and
(c) hydrogen sulfide,
in the presence of (d) a polar solvent.

2. A process according to claim 1 wherein the hydrocarbon-based radical is an aliphatic-based radical and contains up to about 30 carbon atoms.

3. A process according to claim 2 wherein the aliphatic-based radical is alkyl and contains from 3 to about 30 carbon atoms.

4. A process according to claim 3 wherein at least one X is sulfur; at least one X' is oxygen; and each n is 1.

5. A process according to claim 4 wherein a reaction mixture of (a) and (b) in the presence of (d) is first prepared, which is then reacted with (c) at a temperature of 0°–150 °C.

6. A process according to claim 5 wherein (d) is water, organic polar solvents or mixtures thereof.

7. A process according to claim 1 wherein the hexavalent molybdenum oxide compound (b) is an acidic water-soluble hexavalent molybdenum compound that is obtained from molybdenum-trioxide compounds or mixtures of one or more of these compounds.

8. A process according to claim 7 wherein the molybdenum-trioxide compounds are molybdenum trioxide, molybdenum trioxide hydrate, molybdic acid, ammonium molybdates, alkali metal molybdates, or heteropolyacid molybdates.

9. A process according to claim 4 wherein the hexavalent molybdenum oxide compound (b) is an acidic water-soluble hexavalent molybdenum compound that is obtained from molybdenum-trioxide compounds or mixtures of one or more of these compounds.

10. A process according to claim 9 wherein the molybdenum-trioxide compounds are molybdenum trioxide, molybdenum trioxide hydrate, molybdic acid, ammonium molybdates, alkali metal molybdates, or heteropolyacid molybdates.

11. A process according to claim 6 wherein the hexavalent molybdenum oxide compound (b) is an acidic water-soluble hexavalent molybdenum compound that is obtained from molybdenum-trioxide compounds or mixtures of one or more of these compounds.

12. A process according to claim 11 wherein the molybdenum-trioxide compounds are molybdenum trioxide, molybdenum trioxide hydrate, molybdic acid, ammonium molybdates, alkali metal molybdates, or heteropolyacid molybdates.

13. A process according to claim 8 wherein the heteropolyacid molybdates are the phosphomolybdates.

14. A process according to claim 10 wherein the heteropolyacid molybdates are the phosphomolybdates.

15. A process according to claim 12 wherein the heteropolyacid molybdates are the phosphomolybdates.

16. A process according to claim 1 wherein (d) is water.

17. A process according to claim 4 wherein (d) is water.

18. A process according to claim 6 wherein (d) is water.

19. A process according to claim 8 wherein (d) is water.

20. A process according to claim 10 wherein (d) is water.

21. A process according to claim 12 wherein (d) is water.

22. A process according to claim 15 wherein (d) is water.

23. A process according to claim 1 wherein the olefinically unsaturated compound is an olefin defined by the formula $R_1R_2C=CR_3R_4$, wherein each of Rhd 1, $R_2$, $R_3$ and $R_4$ is hydrogen or an organic radical.

24. A process according to claim 23 wherein the olefin contains from about 8 up to about 36 carbon atoms.

25. A process according to claim 23 wherein the olefin is at least one monoolefinic or diolefinic compound; at least one fatty acid ester derived from one or more unsaturated carboxylic acids; or mixtures thereof.

26. A process according to claim 25 wherein the unsaturated carboxylic acids contain from about 16 up to about 20 carbon atoms.

27. A process according to claim 26 wherein the olefin is an α-olefin and contains from about 8 up to about 20 carbon atoms.

28. A process according to claim 26 wherein the fatty acid esters are the fatty oils.

29. A process according to claim 28 wherein the fatty oils are lard oil, peanut oil, cotton seed oil, soybean oil, or corn oil.

30. A process according to claim 28 wherein the fatty oil is soybean oil.

31. A composition prepared according to the process of claim 1.

32. A composition prepared according to the process of claim 4.

33. A compositon prepared according to the process of claim 6.

34. A composition prepared according to the process of claim 10.

35. A composition prepared according to the process of claim 16.

36. A composition prepared according to the process of claim 17.

37. A composition prepared according to the process of claim 18.

38. A composition prepared according to the process of claim 19.

39. A composition prepared according to the process of claim 23.

40. A composition prepared according to the process of claim 25.

41. A composition prepared according to the process of claim 27.

42. A composition prepared according to the process of claim 29.

43. A composition prepared according to the process of claim 30.

44. A lubricant composition comprising a major amount of an oil of lubricating viscosity and a minor amount of at least one composition of claim 31.

45. A lubricant composition comprising a major amount of an oil of lubricating viscosity and a minor amount of at least one composition of claim 32.

46. A lubricant composition comprising a major amount of an oil of lubricating viscosity and a minor amount of at least one composition of claim 33.

47. A lubricant composition comprising a major amount of an oil of lubricating viscosity and a minor amount of at least one composition of claim 34.

48. A lubricant composition comprising a major amount of an oil of lubricating viscosity and a minor amount of at least one composition of claim 35.

49. A lubricant composition comprising a major amount of an oil of lubricating viscosity and a minor amount of at least one composition of claim 36.

50. A lubricant composition comprising a major amount of an oil of lubricating viscosity and a minor amount of at least one composition of claim 37.

51. A lubricant composition comprising a major amount of an oil of lubricating viscosity and a minor amount of at least one composition of claim 38.

52. A lubricant composition comprising a major amount of an oil of lubricating viscosity and a minor amount of at least one composition of claim 39.

53. A lubricant composition comprising a major amount of an oil of lubricating viscosity and a minor amount of at least one composition of claim 40.

54. A lubricant composition comprising a major amount of an oil of lubricating viscosity and a minor amount of at least one composition of claim 41.

55. A lubricant composition comprising a major amount of an oil of lubricating viscosity and a minor amount of at least one composition of claim 42.

56. A lubricant composition comprising a major amount of an oil of lubricating viscosity and a minor amount of at least one composition of claim 43.

57. An additive concentrate comprising about 20-90% of at least one composition of claim 31 and a substantially inert, normally liquid organic diluent.

58. An additive concentrate comprising about 20-90% of at least one composition of claim 32 and a substantially inert, normally liquid organic diluent.

59. An additive concentrate comprising about 20-90% of at least one composition of claim 33 and a substantially inert, normally liquid organic diluent.

60. An additive concentrate comprising about 20-90% of at least one composition of claim 34 and a substantially inert, normally liquid organic diluent.

61. An additive concentrate comprising about 20-90% of at least one composition of claim 35 and a substantially inert, normally liquid organic diluent.

62. An additive concentrate comprising about 20-90% of at least one composition of claim 36 and a substantially inert, normally liquid organic diluent.

63. An additive concentrate comprising about 20-90% of at least one composition of claim 37 and a substantially inert, normally liquid organic diluent.

64. An additive concentrate comprising about 20-90% of at least one composition of claim 38 and a substantially inert, normally liquid organic diluent.

65. An additive concentrate comprising about 20-90% of at least one composition of claim 39 and a substantially inert, normally liquid organic diluent.

66. An additive concentrate comprising about 20-90% of at least one composition of claim 40 and a substantially inert, normally liquid organic diluent.

67. An additive concentrate comprising about 20-90% of at least one composition of claim 41 and a substantially inert, normally liquid organic diluent.

68. An additive concentrate comprising about 20-90% of at least one composition of claim 42 and a substantially inert, normally liquid organic diluent.

69. An additive concentrate comprising about 20-90% of at least one composition of claim 43 and a substantially inert, normally liquid organic diluent.

70. A method for reducing the fuel consumption of an internal combustion engine which comprises lubricating said engine during operation with the lubricant composition of claim 44.

71. A method for reducing the fuel consumption of an internal combustion engine which comprises lubricating said engine during operation with the lubricant composition of claim 45.

72. A method for reducing the fuel consumption of an internal combustion engine which comprises lubricating said engine during operation with the lubricant composition of claim 46.

73. A method for reducing the fuel consumption of an internal combustion engine which comprises lubricating said engine during operation with the lubricant composition of claim 47.

74. A method for reducing the fuel consumption of an internal combustion engine which comprises lubricating said engine during operation with the lubricant composition of claim 48.

75. A method for reducing the fuel consumption of an internal combustion engine which comprises lubricating said engine during operation with the lubricant composition of claim 49.

76. A method for reducing the fuel consumption of an internal combustion engine which comprises lubricating said engine during operation with the lubricant composition of claim 50.

77. A method for reducing the fuel consumption of an internal combustion engine which comprises lubricating said engine during operation with the lubricant composition of claim 51.

78. A method for reducing the fuel consumption of an internal combustion engine which comprises lubricating said engine during operation with the lubricant composition of claim 52.

79. A method for reducing the fuel consumption of an internal combustion engine which comprises lubricating said engine during operation with the lubricant composition of claim 53.

80. A method for reducing the fuel consumption of an internal combustion engine which comprises lubricating said engine during operation with the lubricant composition of claim 54.

81. A method for reducing the fuel consumption of an internal combustion engine which comprises lubricating said engine during operation with the lubricant composition of claim 55.

82. A method for reducing the fuel consumption of an internal combustion engine which comprises lubricating said engine during operation with the lubricant composition of claim 56.

* * * * *

UNITED STATES PATENT AND TRADEMARK OFFICE
CERTIFICATE OF CORRECTION

PATENT NO. : 4,289,635
DATED : September 15, 1981
INVENTOR(S) : Calvin William Schroeck It is certified that error appears in the above–identified patent and that said Letters Patent are hereby corrected as shown below:

Column 18, line 17, "Rhd 1" should read --$R_1$--.

Column 18, line 44, "compositon" should read --composition--.

Signed and Sealed this

Second Day of March 1982

[SEAL]

Attest:

Attesting Officer

GERALD J. MOSSINGHOFF

Commissioner of Patents and Trademarks